United States Patent [19]

Nakamura

[11] Patent Number: 4,961,110

[45] Date of Patent: Oct. 2, 1990

[54] ENDOSCOPE APPARATUS

[75] Inventor: Kazunari Nakamura, Hachioji, Japan

[73] Assignee: Olympus Optical Co., Ltd., Tokyo, Japan

[21] Appl. No.: 376,461

[22] Filed: Jul. 7, 1989

[30] Foreign Application Priority Data

Nov. 2, 1988 [JP] Japan ............................. 63-277917
Apr. 20, 1989 [JP] Japan ............................. 1-101075

[51] Int. Cl.$^5$ ........................... A61B 1/04; A61B 1/06
[52] U.S. Cl. ........................................ 358/98; 128/6; 358/37
[58] Field of Search ..................... 358/98, 37; 128/6

[56] References Cited

U.S. PATENT DOCUMENTS

| | | | |
|---|---|---|---|
| 4,608,597 | 8/1986 | Jaeger | 358/113 |
| 4,695,878 | 9/1987 | Levine et al. | 358/44 |
| 4,766,489 | 8/1988 | Kato | 358/98 |
| 4,875,091 | 10/1989 | Yamada | 358/98 |
| 4,887,153 | 12/1989 | Uehara | 358/98 |

FOREIGN PATENT DOCUMENTS 58-46929 3/1983 Japan .
62-174714 7/1987 Japan .

*Primary Examiner*—Howard W. Britton
*Attorney, Agent, or Firm*—Armstrong, Nikaido, Marmelstein, Kubovcik & Murray

[57] ABSTRACT

This endoscope apparatus comprises an endoscope having at least an image forming optical system, a wavelength separating apparatus separating an observed object image into images of a plurality of wavelength ranges, an imaging apparatus forming an image by an image forming optical system and imaging the images of the respective wavelength ranges separated by the wavelength separating apparatus and a signal processing apparatus forming at least one new image on the basis of the images of at least two wavelength ranges among the images of the respective wavelength ranges imaged by the imaging apparatus and forming an observed image by at least one image including this new image.

23 Claims, 14 Drawing Sheets

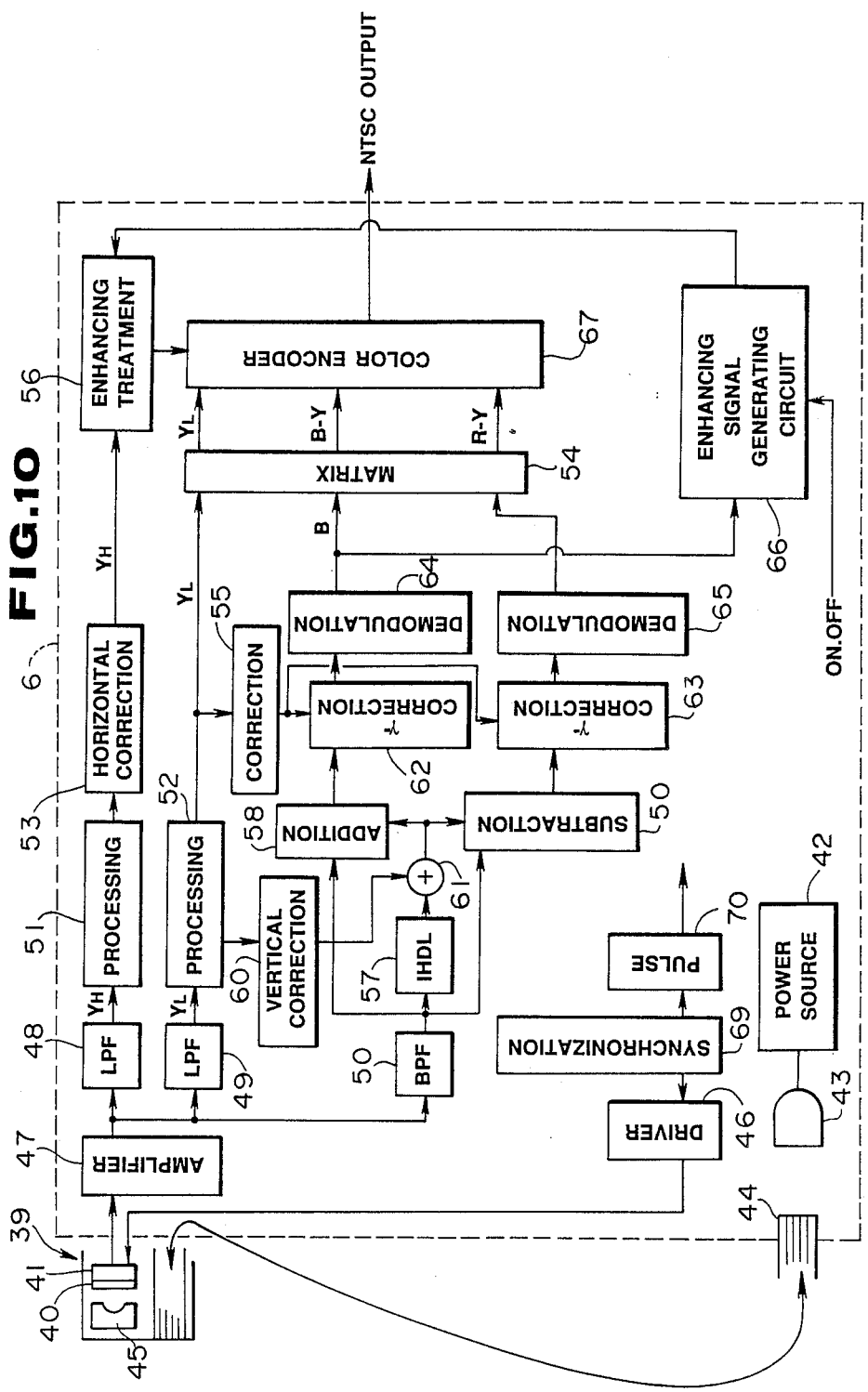

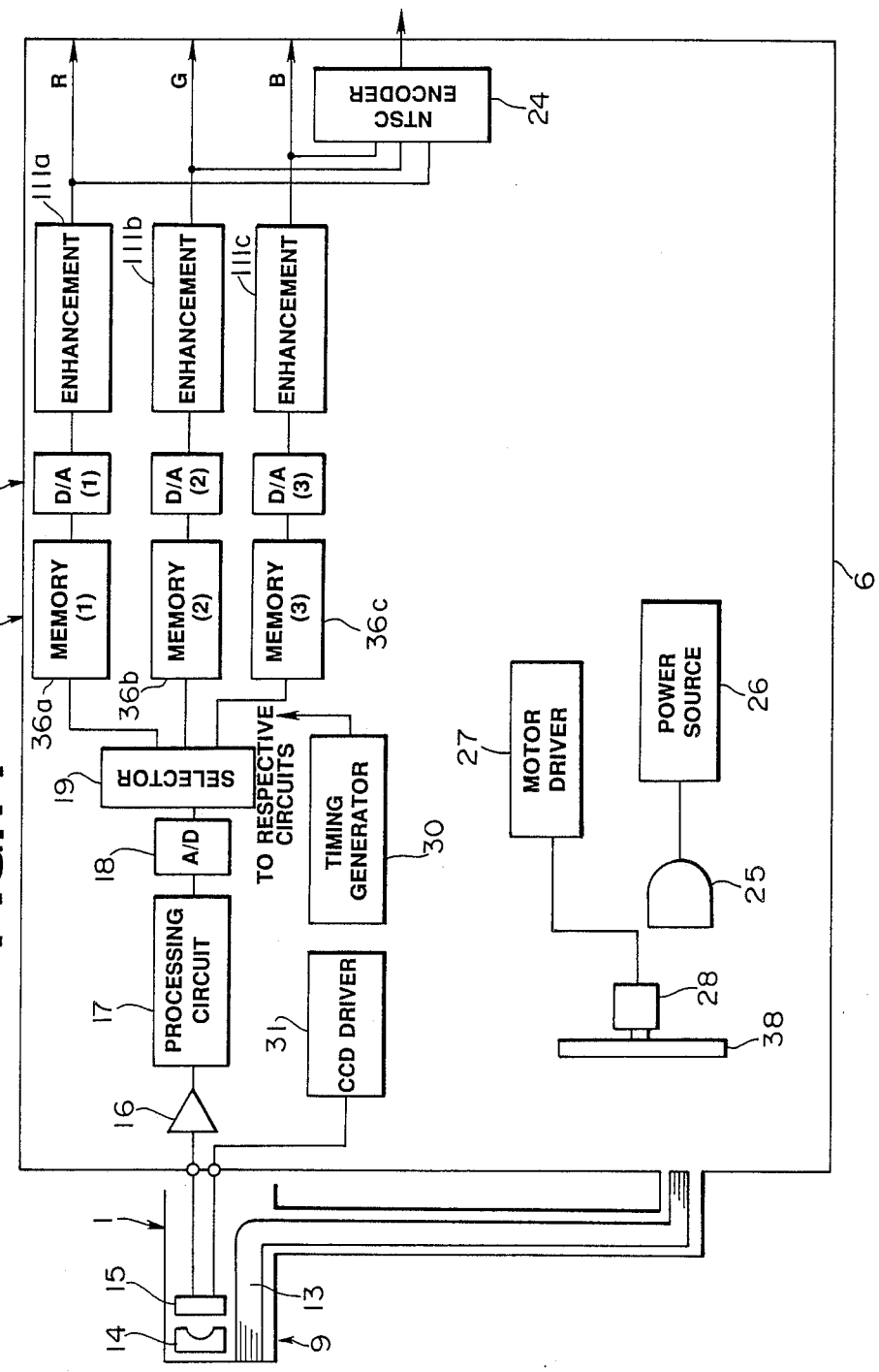

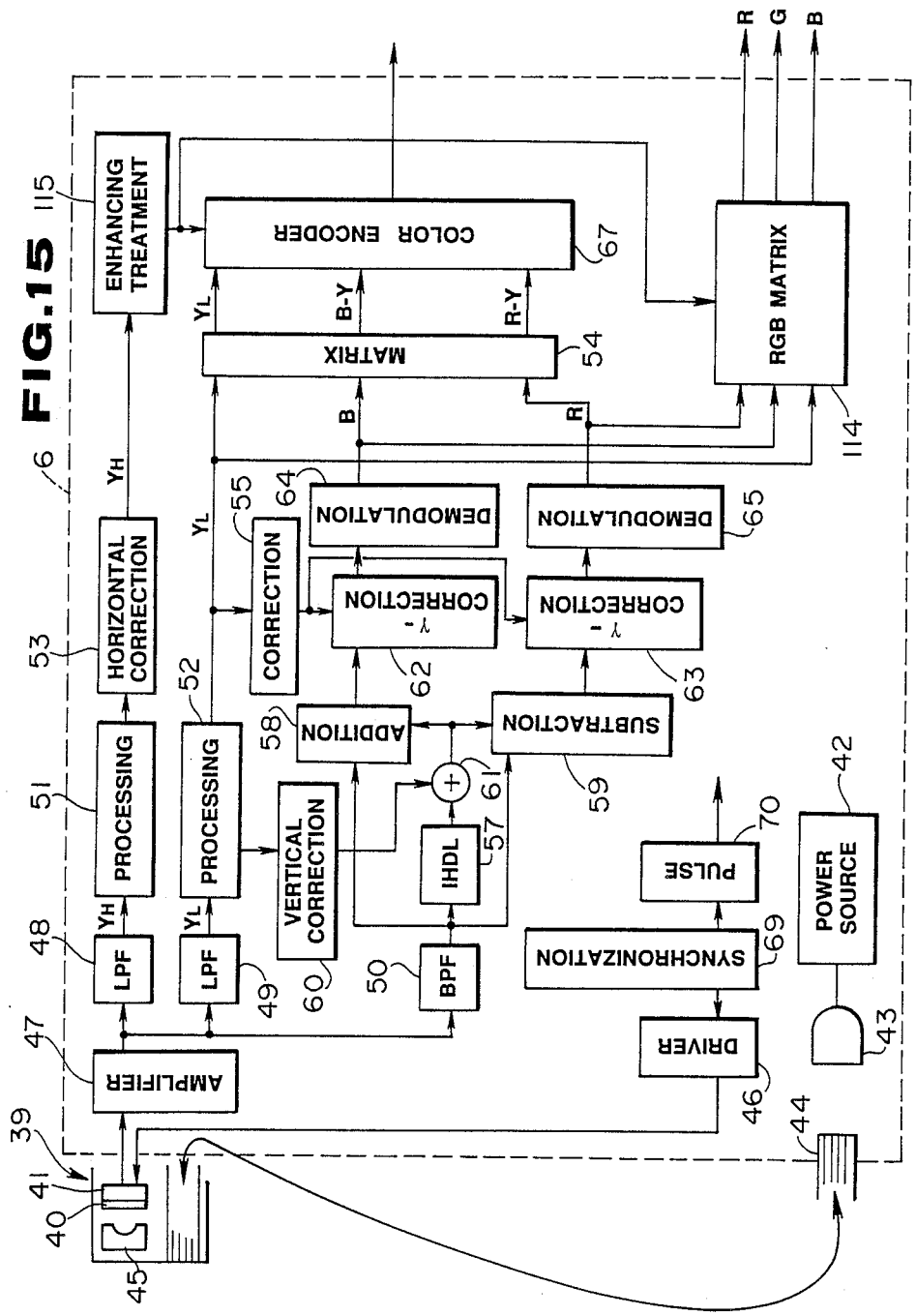

ENDOSCOPE APPARATUS

BACKGROUND OF THE INVENTION:

1. Field of the Invention:

This invention relates to endoscope apparatus and more particularly to an endoscope apparatus wherein any other wavelength ranges than of visible lights can be video-imaged or information obtained by a plurality of wavelength ranges can be video-imaged so that an affected part or a living body information which has not been able to be observed by an ordinary observation may be observed in detail.

2. Related Art Statement:

Recently there is extensively utilized an endoscope whereby, by inserting an elongate insertable part into a body cavity, organs within the body cavity can be observed or, as required, various therapeutic treatments can be made by using treating instruments inserted through a treating instrument channel.

Now, heretofore the body cavity interior has been observed by using an endoscope called a fiber scope but recently it is attempted to video-image any other information than of a visible light range with a solid state imaging device provided at the tip of an insertable part.

In the publication, for example, of a Japanese patent application laid open No. 46929/1983, there is disclosed a technique wherein a video image by near infrared rays is taken in and the part above a fixed level is extracted and is displayed by an outline.

Also, in the publication of a Japanese patent application laid open No. 174714/1987, there is disclosed a technique wherein an image by near infrared rays is quasi-colored to be observable.

However, in the publication of the Japanese patent application laid open No. 46929/1983, there are problems that, not only, as the variation of a near infrared ray picture image is displayed in an outline in a range, it will be difficult to video-image the picture image which is high in the variations of the minute irregularities of the living body surface and the vein image or blood flow picture image below the mucous membrane but also, as only the near infrared rays are all used, no living body information obtained by other wavelengths will be obtained.

Also, in the publication of the above mentioned Japanese patent application laid open No. 174714, there are problems that, as the wavelength of a near infrared range is quasi-colored, as different from the ordinary tone, the orientation will be difficult and the hue variation which is most necessary for the diagnosis of an affected part will not be able to be simultaneously accurately observed. In some case, with only the image of one wavelength range such as the infrared range, a delicate information will not be obtained.

Object and Summary of the Invention:

An object of the present invention is to provide an endoscope apparatus whereby the feature of an object part can be more enhanced.

Another object of the present invention is to provide an endoscope apparatus whereby the feature of an object part can be enhanced and a hue observation similar to an ordinary observation can be also made.

An endoscope apparatus of the present invention comprises an endoscope having at least an image forming optical system, a wavelength separating means separating an object image into a plurality of wavelength range images, an imaging means imaging the images of the respective wavelength ranges formed by the above mentioned image forming optical system and separated by the above mentioned wavelength separating means and a signal processing means forming newly at least one image on the basis of at least two wavelength range images among the respective wavelength range images imaged by the above mentioned imaging means and forming an observed image of at least one image including this new image.

The other features and advantages of the present invention will become apparent enough with the following explanation.

Brief Description of the Drawings:

FIGS. 1 to 6 relate to the first embodiment of the present invention.

FIG. 1 is a block diagram showing the formation of an endoscope apparatus.

FIG. 2 is a side view showing the whole of an endoscope apparatus.

FIG. 3 is an explanatory view showing a rotary filter.

FIG. 4 is a characteristic diagram showing the tramsmittivities of the respective filters of a rotary filter.

FIG. 5 is a characteristic diagram showing the light absorbing characteristics of an ICG.

FIG. 8 is an explanatory view showing the formation of an endoscope apparatus.

FIG. 9 is a characteristic diagram showing the spectral characteristic of the light absorbing degree of hemoglobin.

FIGS. 10 to 13 relate to the fourth embodiment of the present invention.

FIG. 10 is a block diagram showing the formation of an endoscope apparatus.

FIG. 11 is an explanatory view of a color filter array.

FIG. 12 is a characteristic diagram showing the transmittive characteristics of the respective filters of a color filter array.

FIG. 13 is a characteristic diagram showing absorption spectra of skin coloring matters.

FIGS. 14 to 16 relate to the fifth embodiment of the present invention.

FIGS. 14 and 15 are block diagrams showing schemmatic formations of endoscope apparatus.

FIG. 16 is a block diagram showing a signal processing circuit which is an essential part of this embodiment.

Detailed Description of the Preferred Embodiments:

The first embodiment of the present invention is shown in FIGS. 1 to 6.

Figure 2:
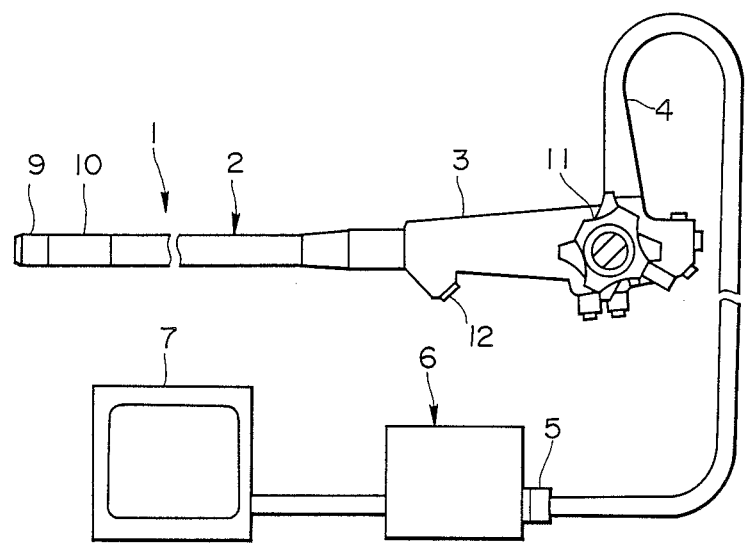

As shown in FIG. 2, the endoscope apparatus of this embodiment is provided with an electronic endoscope 1. This electronic endoscope 1 has an elongate and, for example, flexible insertable part 2 at the rear end of which a thick operating part 3 is provided. A flexible universal cord 4 is extended sidewise from the rear end part of the above mentioned operating part 3 and is provided at the tip with a connector 5. The above mentioned electronic endoscope 1 is to be connected through the above mentioned connector 5 to a video processor 6 having a light source apparatus and signal processing circuit built-in. Further, the above mentioned video processor 6 is to be connected with a monitor 7.

A rigid tip part 9 and a curvable part 10 adjacent to this tip part 9 and curvable on the rear side are sequentially provided on the tip side of the above mentioned insertable part 2. By rotating and operating a curving operation knob 11 provided on the above mentioned operating part 3, the above mentioned curvable part 10 can be curved horizontally or vertically. The above mentioned operating part 3 is provided with an inserting port 12 communicating with a treating instrument channel provided through the above mentioned insertable part 2.

Figure 1:
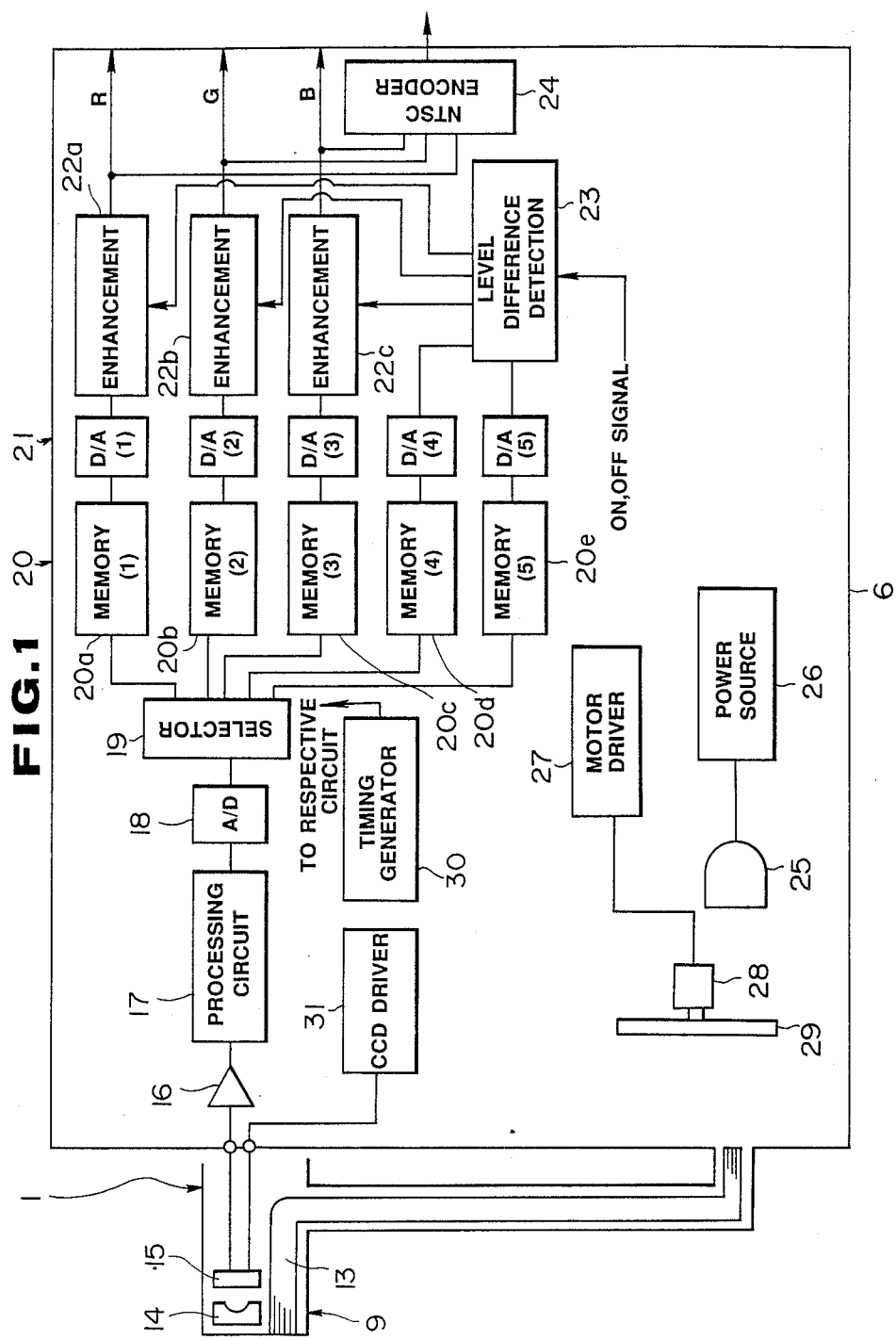

As shown in FIG. 1, a light guide 13 consisting of a fiber bundle leading a light into a body cavity from the connector 5 to the tip part 9 through the above mentioned electronic endoscope 1. An image forming lens 14 forming an optical image of a light returning from an observed part of an inside wall or the like of a body cavity illuminated by an illuminating light transmitted through the above mentioned light guide 13 and a CCD 15 which is a solid state imaging device photoelectrically converting the optical image formed by this lens 14 are provided in the above mentioned tip part 9. A signal line connected to the above mentioned CCD 15 is inserted through the insertable part 2, operating part 3 and universal cord 4 and is connected to the above mentioned connector 5.

On the other hand, a CCD driver 31 driving the above mentioned CCD 15 and a pre-amplifier 16 amplifying a signal read out of the CCD 15 driven by this CCD driver 31 are provided within the above mentioned video processor 6. A processing circuit 17 processing to white-balance and γ-correct the signal amplified by the pre-amplifier 16 so as to be a video signal is provided in the step after the above mentioned pre-amplifier 16. An A/D converter 18 converting the signal processed by this processing circuit 17 to a digital signal is provided in the step after this processing circuit 17. A selector 19 sequentially selecting the picture images of the respective wavelength ranges read out in time series is provided in the step after this A/D converter 18. A memory group 20 of five picture surfaces is provided in the step after this selector 19 so that the signals sequentially selected by the above mentioned selector 19 may be sequentially memorized in the respective memories (1) 20a to (5) 20e of the above mentioned memory group 20. A D/A converter group 21 consisting of five D/A converters (1) to (5) converting to analogue signals and synchronizing the picture image signals read out of the respective memories is provided in the step after the above mentioned memories (1) 20a to (5) 20e. A level difference detecting circuit 23 detecting the level difference between the outputs of the D/A converter (4) and D/A converter (5) is provided in the step after the D/A converters (4) and (5) of the above mentioned D/A converter group 21. Enhancing circuits 22a, 22b and 22c enhancing the respective signals of R, G and B on the basis of the level difference detected by the above mentioned level difference detecting circuit 23 are provided reapectively in the steps after the above mentioned D/A converters (1) to (3). The outputs of the above mentioned enhancing circuits 22 (representing 22a, 22b and 22c) are output as R, G and B signals and are converted to an NTSC signal to be output.

Figure 3:
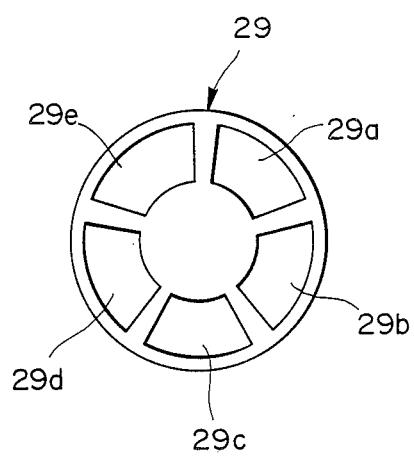
Figure 4:
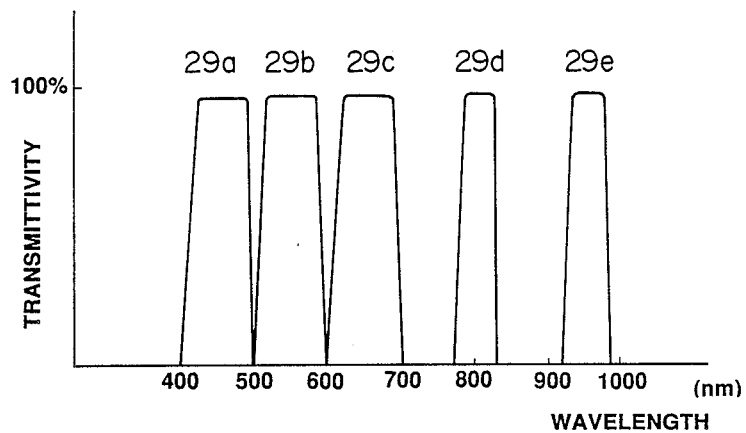
Figure 5:
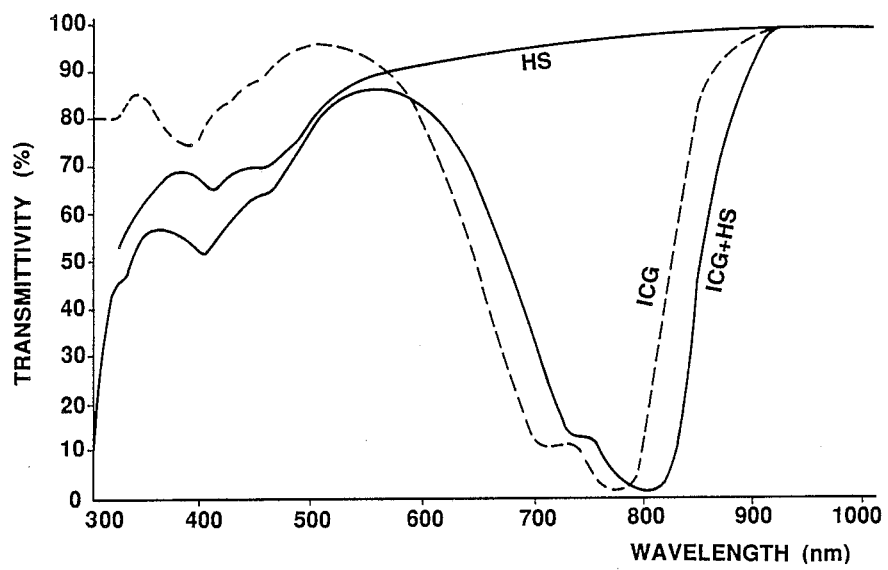

On the other hand, on the light source apparatus side within the video processor 6, there are provided a lamp 25 emitting lights in a wide band from ultraviolet rays to visible lights, a power source feeding electric power to this lamp 25, a rotary filter 29 separating the light emitted from the above mentioned lamp 25 into colors of wavelength widths of narrow bands, a motor rotating and driving this rotary filter 29 and a motor driver 27 controlling this motor 28. As shown in FIG. 3, in the above mentioned rotary filter 29, five kinds of filters 29a to 29e are arranged in the peripheral direction so that the light may be separated into colors of five kinds of wavelength ranges. The transmittive characteristics of the respective filters 29a to 29e are shown in FIG. 4. The filters 29a, 29b and 29c respectively transmit the respective wavelength ranges of R, G and B, the filter 29d transmits a wavelength range with 805 nm as a center and the filter 29e transmits near infrared rays near 900 to 1000 nm.

Also, a timing generator 30 generating a timing between the respective circuits is provided within the video processor.

The operation of this embodiment shall be explained in the following.

The light emitted from the lamp 25 is time-serially separated into colors by the rotary filter 29. Here, as shown in FIGS. 3 and 4, as the rotary filter 29 can separate the light into colors of five kinds of wavelength ranges, the light led into a body cavity by the light guide 13 will be separated into the colors of the respective visible light ranges of R, G and B, the light with 805 nm as a center and the near infrared rays of 900 to 100 nm and will be radiated to a living body.

Here, in case a coloring matter of Indo Cyanine Green (ICG) is mixed into a blood, for example, by an intravenous injection, the maximum absorption peak will be obtained at 805 nm but the infrared rays above 900 nm will show no change by mixing in the ICG. By the way, in FIG. 5, HS represents the transmittivity curve of a solution ($\times$10.1 cm) of a serum of a human blood, ICG represents that of an ICG solution (0.1 mg/dl·1 cm), ICG+HG represents that of a solution (0.1 mg/dl·1 cm$\times$10) of ICG and a human blood).

The light reflected by the living body is made to form an image by the lens 14 and is photoelectrically converted by the CCD 15. The respective picture images of R, G and B and two kinds of near infrared picture images corresponding to the filters 29a to 29e and time-serially read out by the selector 19 through the pre-amplifier 16, processing circuit 17 and A/D converter are memorized in the respective memories (1) 29a to (5) 29e and are converted to synchronized analogue signals by the D/A converter group 21. Among them, the R, G and B signals output from the D/A converters (1) to (3) are input respectively into the enhancing circuits 22a to 22c and the two kinds of near infrared picture image signals output from the D/A converters (4) and (5) are input into the level difference detecting circuit 23.

Here, as the difference between the light absorbing degrees of the two kinds of near infrared rays represents a vein part and is of near infrared rays, the living body transmittivity will be higher than in the visible light range and the vein image below the mucous membrane or the concentration degree of hemoglobin difficult to observe with visible lights will be shown.

Therefore, the difference between the two wavelengths detected by the level difference detecting circuit 23 is a living body information below the mucous membrane difficult to observe with visible lights. The respective signals of R, G and B are processed to be enhanced in the enhancing circuits 22a, 22b and 22c with the signal detected by this level difference detecting circuit 23. As shown, for example, in FIG. 6(a), the above mentioned enhancing circuit 22 is formed of an analogue multiplier 101 to operate a product X.Y/SF (wherein SF is a scale factor) of the respective signals (X) of R, G and B and the enhancing signal (Y) which is a level difference to make an enhancing process.

The respective picture image signals of R, G and B thus processed to be enhanced are output directly as R, G and B signals or are output as converted to an NTSC signal by an NTSC encoder 24.

Thus, in this embodiment, when the respective picture images of R, G and B forming a color picture image among picture images of a plurality of wavelength ranges separated by the rotary filter 29 and imaged by the CCD 15 are enhanced in response to the variation of the difference of the picture images of the other two kinds of near infrared ranges among the picture images of the above mentioned plurality of wavelength ranges, new R, G and B picture images will be formed and a color observed image will be formed of these new R, G and B picture images. In other words, the luminance of the color observed image is enhanced in response to the variation of the difference of the picture images of the above mentioned two kinds of near infrared ranges.

Therefore, a tone similar to that of an ordinary observed picture image can be observed and the running state of the vein below the mucous membrane and the variation of the distribution of hemoglobin which have been difficult to observe with the observation of an ordinary visible light range can be observed as picture images of a high contrast and the diagnosability will be improved.

Figure 6A:
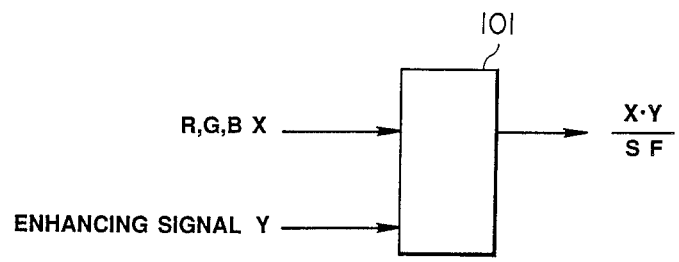
FIGS. 6(a) to (c) are circuit diagrams showing respectively enhancing circuits.
Figure 6B:
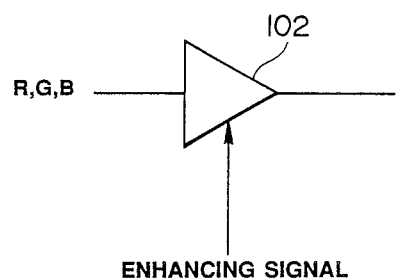
Figure 6C:
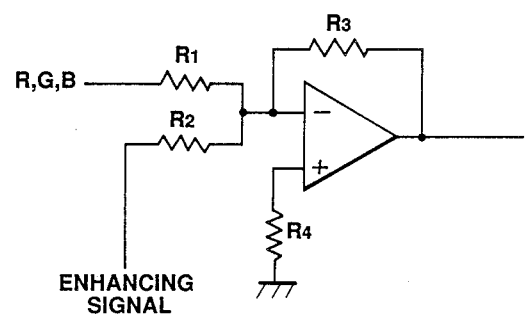

By the way, the enhancing circuit 22 is not only the one shown in FIG. 6(a) but also may be formed of such gain controlling amplifier 102 as is shown in FIG. 6(b) so as to control the gains of the respective signals of R, G and B with the enhancing signal. Also, as shown in FIG. 6(c), the enhancing signal may be added to the respective signals of R, G and B. The circuit shown in FIG. 6(c) is an adding circuit which is negatively fed back by a resistance $R_3$ and in which the respective signals of R, G and B and enhancing signal are input respectively through resistances $R_1$ and $R_2$ into an inverted input end of an operating amplifier 103 earthed at a non-inverted input end through a resistance $R_4$.

Also, as shown in FIG. 1, by switching on/off from outside the level difference detecting circuit 23 with an on/off signal, it is possible to obtain a perfect visible picture image (ordinary observed picture image).

Figure 7:
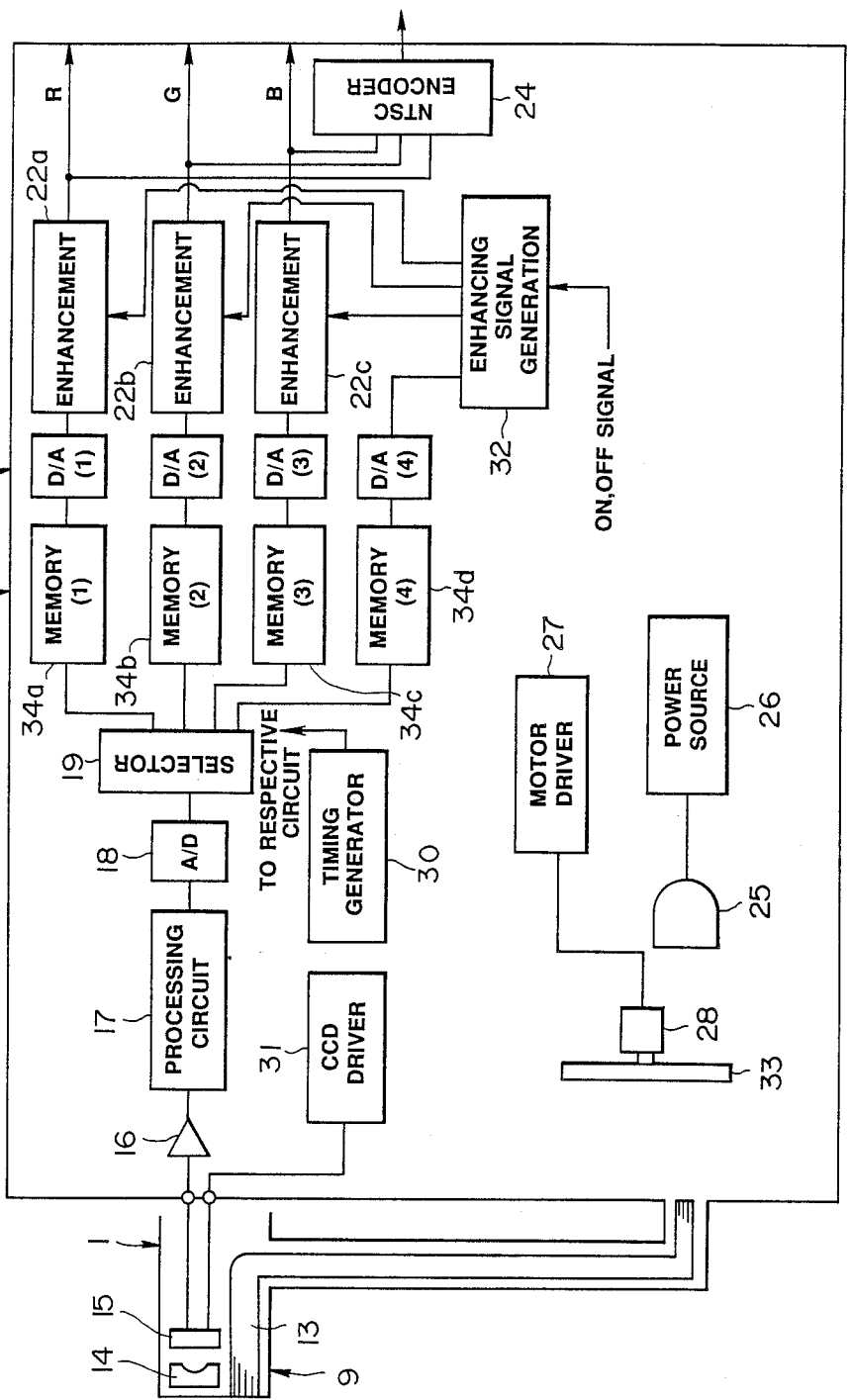
FIG. 7 is a block diagram showing the formation of an endoscope apparatus of the second embodiment of the present invention.

The second embodiment of the present invention is shown in FIG. 7.

In this embodiment, a rotary filter 33 separating colors into R, G and B and near infrared rays with 805 nm as a center is provided instead of the rotary filter 29 of the first example. Also, a memory group 34 consisting of four memories (1) 34a to (4) 34d is provided instead of the memory group 20 and a D/A converter group 35 consisting of four D/A converters is provided instead of the D/A converter group 21. Also, an enhancing signal generating circuit 32 is provided instead of the level difference detecting circuit 23.

In this embodiment, the respective video signals of R, G and B video imaged the same as in the first embodiment and the video signal of the near infrared rays with 805 nm as a center color-separated by the rotary filter 33 are made simultaneous by the memory group 34 and D/A converter 35. Here, as the video image of the near infrared rays with 805 nm as a center greatly varies in the light absorbing degree by the intravenous injection of ICG the same as in the first embodiment, an enhancing signal is generated in the enhancing signal generating circuit 32 from this near infrared video signal and, the same as in the first embodiment, the respective signals of R, G and B are processed to be enhanced.

According to this embodiment, the formation of the rotary filter, memory group and converter group is simplified.

The other formations, operations and effects are the same as in the first embodiment.

Figure 8:
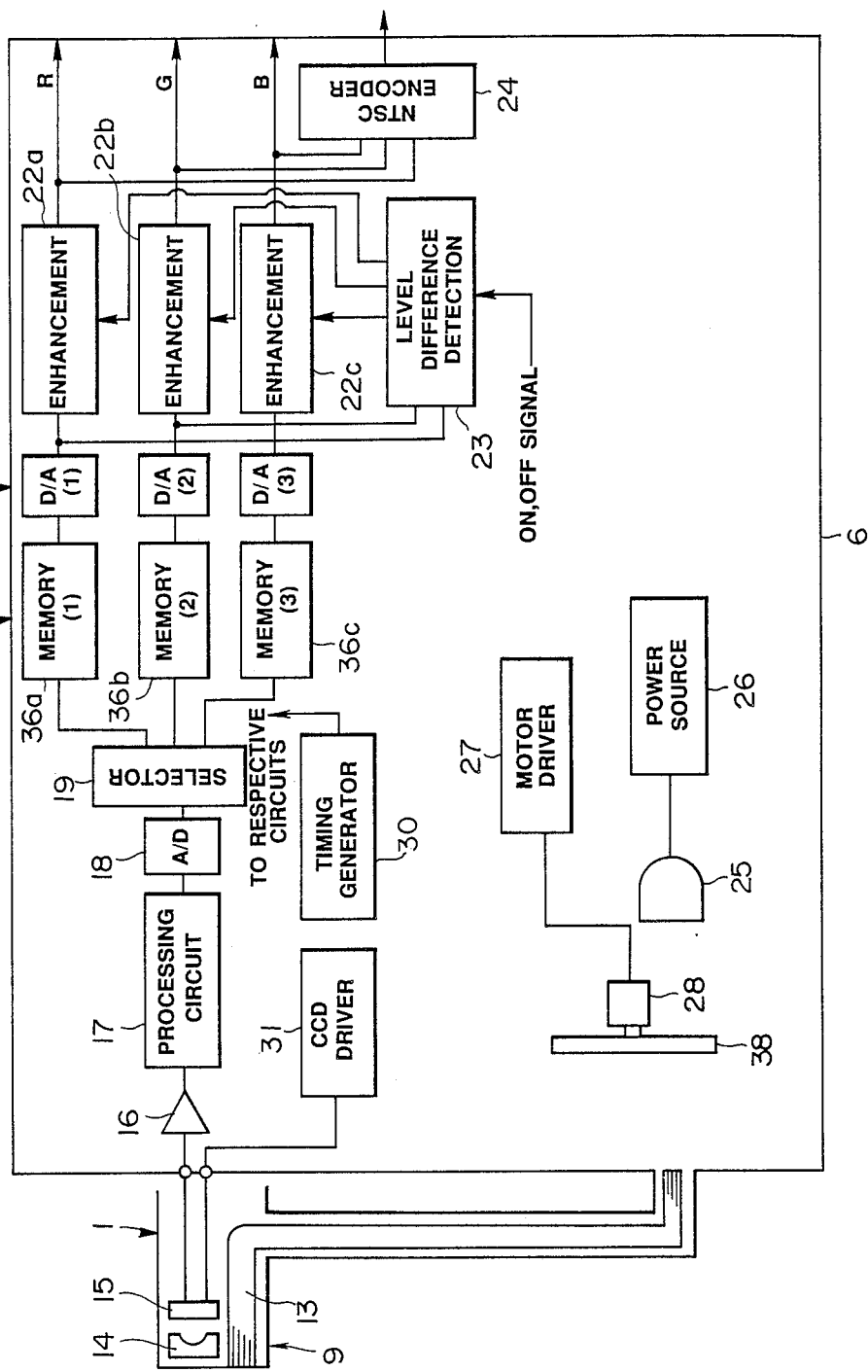
FIGS. 8 and 9 relate to the third embodiment of the present invention.
Figure 9:
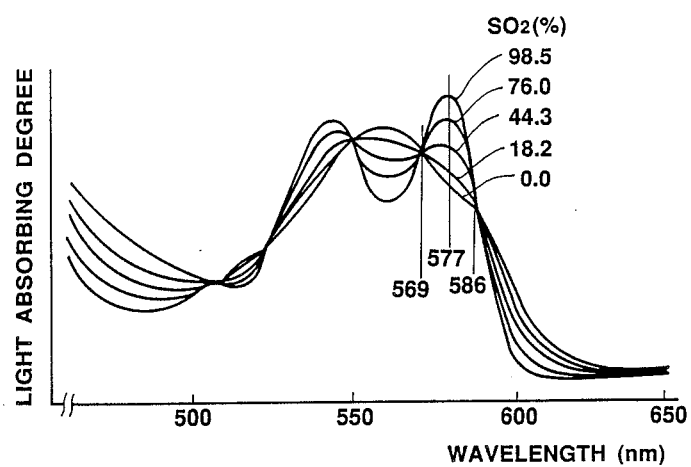
Figure 13:
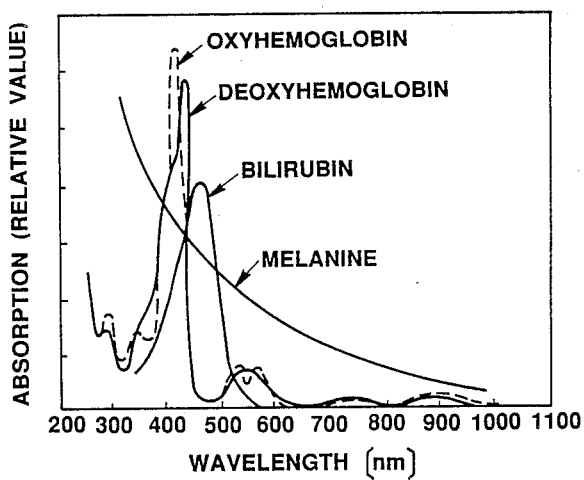

The third embodiment of the present invention is shown in FIGS. 8 and 9.

In this embodiment, a rotary filter 38 color-separating the three wavelength ranges of R, G and B to obtain an ordinary visible picture image is provided instead of the rotary filter 29 of the first embodiment. A memory group 36 replacing the memory group 20 is formed of three memories (1) 36a to (3) 36c so as to be able to memorize the video images of the respective wavelength ranges of R, G and B color-separated by the above mentioned rotary filter 38. In the same manner, a D/A converter group 37 replacing the D/A converter group 21 is formed of three D/A converters (1) to (3).

The level difference detecting circuit 23 is of the same formation as in the first embodiment but is formed in this embodiment to detect the level difference between R and G from the memories (1) 36a and (2) 36b.

In this embodiment, the same as in the first embodiment, a picture image within a body cavity is to be obtained. Here, the spectral characteristics of the light absorbing degree of hemoglobin occupying the greater part of the color of a membrane of a living body are as shown in FIG. 9. As the amount of hemoglobin is substantially proportional to the variation of its light absorbing degree, the difference between the G and R components large in the variation amount is detected by the level difference detecting circuit 23 and, with this level difference as an enhancing signal, the picture image is processed to be enhanced in response to the hemoglobin amount by the enhancing circuit 22 so as to be made a video image.

By the way, in FIG. 9, $SO_2$ represents an oxygen saturated degree of hemoglobin.

According to this embodiment, at the normal observing time, the variation of the tone difference with the slightest variation of the blood amount is processed to be enhanced, the detecting capacity is improved, the variation of the hemoglobin distribution can be observed with a picture image of a high contrast and therefore there is an effect of the improvement of the diagnosability.

The other formations, operations and effects are the same as in the first embodiment.

The fourth embodiment of the present invention is shown in FIGS. 10 to 13.

The electronic endoscope 39 in this embodiment is of a simultaneous system using a CCD 41 having a color filter array 40.

A light source part within the video processor 6 has a lamp 43 made to emit a light by a power source 42. The light emitted from this lamp 43 is led to the tip part of the insertable part by a light guide 44 of the electronic endoscope 39 and is radiated to an object to be imaged.

Figures 11, 12:
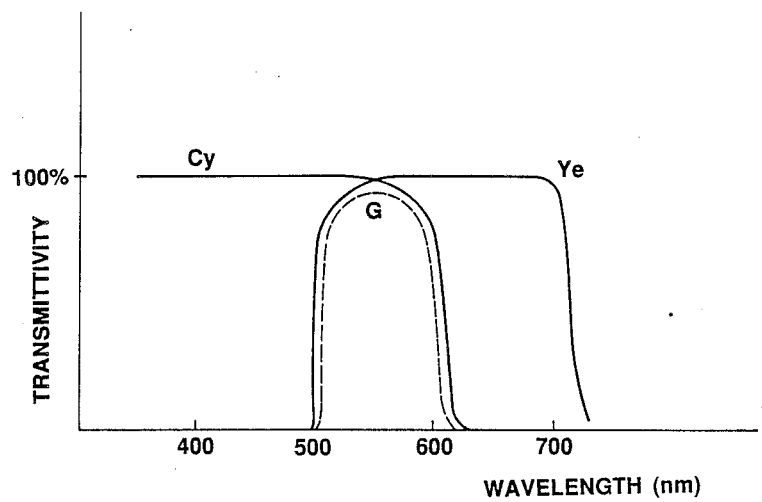

The optical image of the illuminated object is made to form an image on the imaging surface of the CCD 41 by an objective lens 45 and, in such case, is color-separated by a color filter array 40 in which, as shown in FIG. 11, color transmitting filters of three colors of G (green), Cy (cyan) and Ye (yellow) are arranged in the form of a mosaic. The transmittive characteristics of the respective filters of G, Cy and Ye are shown in FIG. 12.

The output of the above mentioned CCD 41 is read out by the application of a driving signal from a driver 46, is amplified by an amplifier 47 within the video processor 6 and is then passed through LPFs 48 and 49 and BPF 50. The above mentioned LPFs 48 and 49 show cutoff characteristics, for example, of 3 MHz and 0.8 MHz. The signal passed respectively through these is divided into a luminance signal $Y_H$ of a high band and a luminance signal $Y_L$ of a low band which are input respectively into processing circuits 51 and 52 and have $\gamma$ and the like corrected. The luminance signal $Y_H$ on the high band side passed through the above mentioned processing circuit 51 has the horizontal outline and horizontal aperture corrected in a horizontal correcting circuit 53 and is then input into an enhancing processing circuit 56.

The luminance signal $Y_L$ on the low band side passed through the process circuit 52 is input into a matrix circuit 54 for displaying a video image and has tracking corrected.

On the other hand, the color signal component is extracted by passing through the BPF 50 of the band passing 3.58±0.5 MHz. This color signal component is input into a 1HDL (1H delay line) 57, adder 58 and subtracter 59 and color signal components B and R are separated and extracted. By the way, in this case, the output of the 1HDL 57 is processed in the processing circuit 52a and is further mixed in a mixer 61 with the luminance signal $Y_L$ on the low band side having had the vertical aperture corrected in a vertical correcting circuit 60 and this mixed output is input into the above mentioned adder 58 and subtracter 59. The color signal B of the adder 58 and the color signal R of the subtracter 59 are input respectively into $\gamma$-correcting circuits 62 and 63, are $\gamma$-corrected by using the luminance signal $Y_L$ on the low band side passed through the correcting circuit 55, are input respectively into demodulators 64 and 65, are made demodulated color signals B and R and are then input into a matrix circuit 54.

On the other hand, the B signal demodulated by the demodulator 64 is input into an enhanced signal generating circuit 66 and the enhanced signal from this enhanced signal generating circuit 66 is input into an enhancing processing circuit 56.

Also, color difference signals R-Y and B-Y are produced by a matrix circuit 54 and are then input into a color encoder 67. A luminance signal produced by mixing the luminance signals $Y_L$ and $Y_H$ and a chroma signal produced by rectangularly demodulating the color difference signals R-Y and B-Y with a subcarrier are mixed, further a synchronizing signal is superimposed and a composite video signal is output from the NTSC output end 68.

By the way, a synchronizing signal is input by a synchronizing signal generating circuit 69 into a driver 46 outputting a driving signal synchronized with the synchronizing signal. The output of this synchronizing signal generating circuit 69 is input into a pulse generator 70 which outputs various timing pulses.

In this embodiment formed as in the above, an ordinary color difference signal is obtained from the matrix circuit 54 and is input into the color encoder 67. On the other hand, as clear from FIG. 13, various coloring matters (oxyhemoglobin, deoxyhemoglobin, bilirubin, melanine, etc.) increase in the light absorbing degree in the B or ultraviolet range. That is to say, the picture image in the B or ultraviolet range can obtain a picture image of a high contrast on a small amount of a coloring matter.

Therefore, in this embodiment, the B signal output from the demodulating circuit 64 is made an enhancing processing signal by the enhancing signal generating circuit 66, is processed to be enhanced by the the same enhancing processing circuit 56 as in the first embodiment and is input into the color encoder 67 to obtain a picture image for a very small amount of a coloring matter variation on the surface of a mucous membrane.

Thus, according to this embodiment, as the observation is possible with the tone similar to that of the ordinary picture image and by processing the ordinary luminance signal to be enhanced by the B component having little influence, it is possible to obtain a picture image of a high contrast on the fine unevenness of a mucous membrance surface and the variation of a coloring matter amount or particularly the red generation of a slight affected part by the concentration of hemoglobin and there is an effect of the improvement of the diagnosability.

By the way, in the first to fourth embodiments, in the enhancing process, not only the variation of the thickness but also the variation of the chroma may be enhanced in so far as the color picture image does not become unnatural, that is to say, the diagnosis is not ill influenced.

Figure 16:
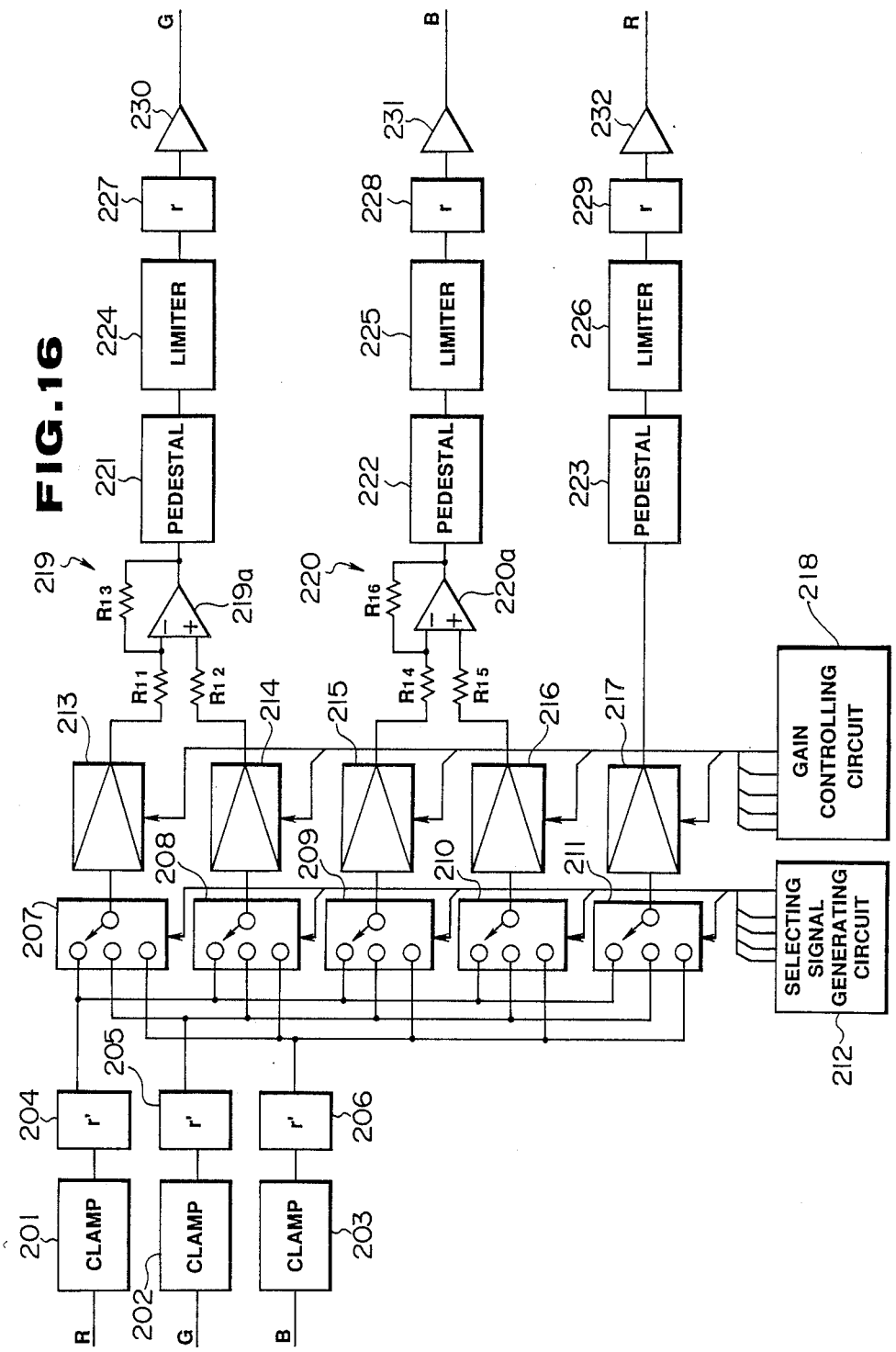

The fifth embodiment of the present invention is shown in FIGS. 14 to 16.

In this embodiment, the picture image signals of R, G and B output from such general endoscope apparatus as is shown in FIG. 14 or 15 are further input and processed in such signal processing circuit as is shown in FIG. 6.

The endoscope apparatus shown in FIG. 14 is not provided with the level difference detecting circuit 23 in the endoscope apparatus shown in FIG. 8 and is provided with enhancing circuits 111a, 111b and 111c which enhance general outlines but are not always necessary instead of the enhancing circuits 22a, 22b and 22c.

The endoscope apparatus shown in FIG. 15 is not provided with the enhancing signal generating circuit 66 in the endoscope apparatus shown in FIG. 10, is provided with R, G and B outputs and is also provided with an enhancing circuit 115 which enhances general outlines but is not always necessary. In this apparatus, luminance signals $Y_L$ and $Y_H$ and color signals B and R demodulated by demodulators 64 and 65 are input into an RGB matrix circuit 114 and R, G and B signals are produced by this RGB matrix 114.

The signal processing circuit shown in FIG. 16 is provided with clamping circuits 201, 202 and 203 clamping the respective input video signals of R, G and B so that the signals clamped by these clamping circuits 201 to 203 may be input respectively into γ'-circuits 204, 205 and 206 whereby the signal γ-corrected so as to be displayed in a television picture surface or the like in such endoscope apparatus as is shown in FIG. 14 or 15 is γ-corrected (such γ-correction shall be also called a γ'-correction hereinafter) so that the picture image signal level and the brightness of the video image may be in a linear relation. Five selector circuits 207, 208, 209, 210 and 211 selecting the optimum video signals among the respective video signals of R, G and B are provided in the steps after the above mentioned γ'-circuits 204 to 206. The respective selector circuits 207 to 211 have respectively three input ends and one output end and the respective outputs of the above mentioned γ'-circuits 204, 205 and 206 are to be input respectively into the three input ends. The above mentioned selector circuits 207 to 211 are controlled in selecting signals by a selecting signal from a selecting signal generating circuit 212. The outputs of the above mentioned respective selector circuits 207 to 211 are input respectively into gain variable amplifiers 213, 214, 215, 216 and 217 so that the level of the signal may be variable. The above mentioned gain variable amplifiers 213 to 217 are controlled in the gain respectively by a gain controlling circuit 218.

The outputs of the above mentioned gain variable amplifiers 213 and 214 are input into a differential amplifying circuit 219 to operate the difference between both outputs. In the above mentioned differential amplifying circuit 219, the outputs of the gain variable amplifiers 213 and 214 are applied respectively through resistances $R_{11}$ and $R_{12}$, to the respective input ends of an operating amplifier 219a negatively fed back through a resistance $R_{13}$.

Also, the outputs of the above mentioned gain variable amplifiers 215 and 216 are input into a differential amplifying circuit 220 to operate the difference between both outputs. In the above mentioned differential amplifying circuit 220, the outputs of the gain variable amplifiers 215 and 216 are applied respectively through resistances $R_{14}$ and $R_{15}$ to the respective input ends of an operating amplifier 220a negatively fed back through a resistance $R_{16}$.

The respective outputs of the above mentioned differential amplifying circuits 219 and 220 and gain variable amplifier 217 are input respectively into pedestal level setting circuits 221, 222 and 223 setting pedestals of video signals. The respective outputs of the above mentioned pedestal level setting circuits 221 to 223 are input respectively into limiter circuits 224, 225 and 226 defining the output level widths of video signals. The respective outputs of the above mentioned limiter circuits 224 to 226 are input respectively into γ-correcting circuits 227, 228 and 229 making γ-corrections to be output to a television picture surface. The respective outputs of the above mentioned γ-correcting circuits 227 to 229 are output as video signals of G, B and R respectively through buffer circuits 230, 231 and 232.

The operation of this embodiment shall be explained in the following.

The video signals of R, G and B output from such general field sequential type electronic endoscope apparatus as is shown in FIG. 14 or such general simultaneous type electronic endoscope apparatus as is shown in FIG. 15 are input into a signal processing circuit shown in FIG. 16.

The input video signals are clamped by the clamping circuits 201 to 203 and are input into the γ'-circuits 204 to 206. The signals γ-corrected in the electronic endoscope apparatus are inversely corrected (γ'-corrected) in response to the respective levels and are γ-corrected so that the video signal level and the brightness of the video image may be in a linear relation.

Next, one of the respective signals of R, G and B is selected by the respective selecting circuits 207 to 211 in response to the signal generated by a selecting signal generating circuit 212. Here, as an example, as described in the third embodiment, a G signal well showing the distribution of hemoglobin on a mucous membrane and an R signal varying little are selected respectively by the selecting circuits 207 and 208, the gains of variable gain amplifiers 213 and 214 are designated by a gain controlling circuit 218, the G and R signals are amplified with these gains by the above mentioned variable gain amplifiers 213 and 214 and thereby the above mentioned G and R signals are multiplied by a predetermined coefficient.

Also, in a general mucous membrane surface, the G and B signals high in the correlation between the picture images are selected by selector circuits 209 and 210 and are multiplied by a predetermined coefficient by variable gain amplifiers 215 and 216 the same as is described above.

The outputs of the above mentioned variable gain amplifiers 213 and 214 are input into the differential amplifying circuit 219 and the level difference between the video signals is processed to be operated. Also, the level difference between the video signals which are the outputs of the variable gain amplifiers 215 and 216 is processed to be operated by the differential amplifying circuit 220. The two video signals obtained by thus operating the level difference are adjusted in the pedestal levels by the pedestal level setting circuits 221 and 222 so that the above mentioned level difference may be displayed to be maximum and the average value of the signal levels may be substantially equal to the average value of the video signals at the displaying time. The video signals thus adjusted in the pedestal levels are limited to be within the displayable signal level range by the limiter circuits 224 and 225, are γ-corrected by the γ-correcting circuits 227 and 228 and are output respectively as video signals of G and B through the buffer circuits 230 and 231.

On the other hand, the R signal forming the tone of the entire mucous membrane surface is selected by the selector circuit 211 and is input into the variable gain amplifier 217 in which a gain is set so that no sense of difference may be given to the tone at the final displaying time in the television monitor. The output of this variable gain amplifier 217 is adjusted in the pedestal level by the pedestal level setting circuit 223, is limited by the limiter circuit 226 to be within the displayable signal level range, is γ-corrected by the γ-correcting circuit 229 to be displayed in the television monitor and is output as a video signal through the buffer circuit 232.

According to this embodiment, as the difference between the G signal and R signal can be displayed, a red generating part of a delicate tone difference will be able to be detected and also as the difference between the G and B signals high in the correlation can be enhanced and displayed, a fine affected part will be able to be detected. Thereby, there is an effect that the diagnosability is improved.

Also, the boundary or the like of a slight dyeing at the time of dyeing with methylene blue or the like can be processed to be enhanced at a real time.

By the way, in this embodiment, when a log amplifier is provided in the gain amplifier, it will be possible to obtain picture image data proportional to the concentrations of the respective coloring matters.

Figure 17:
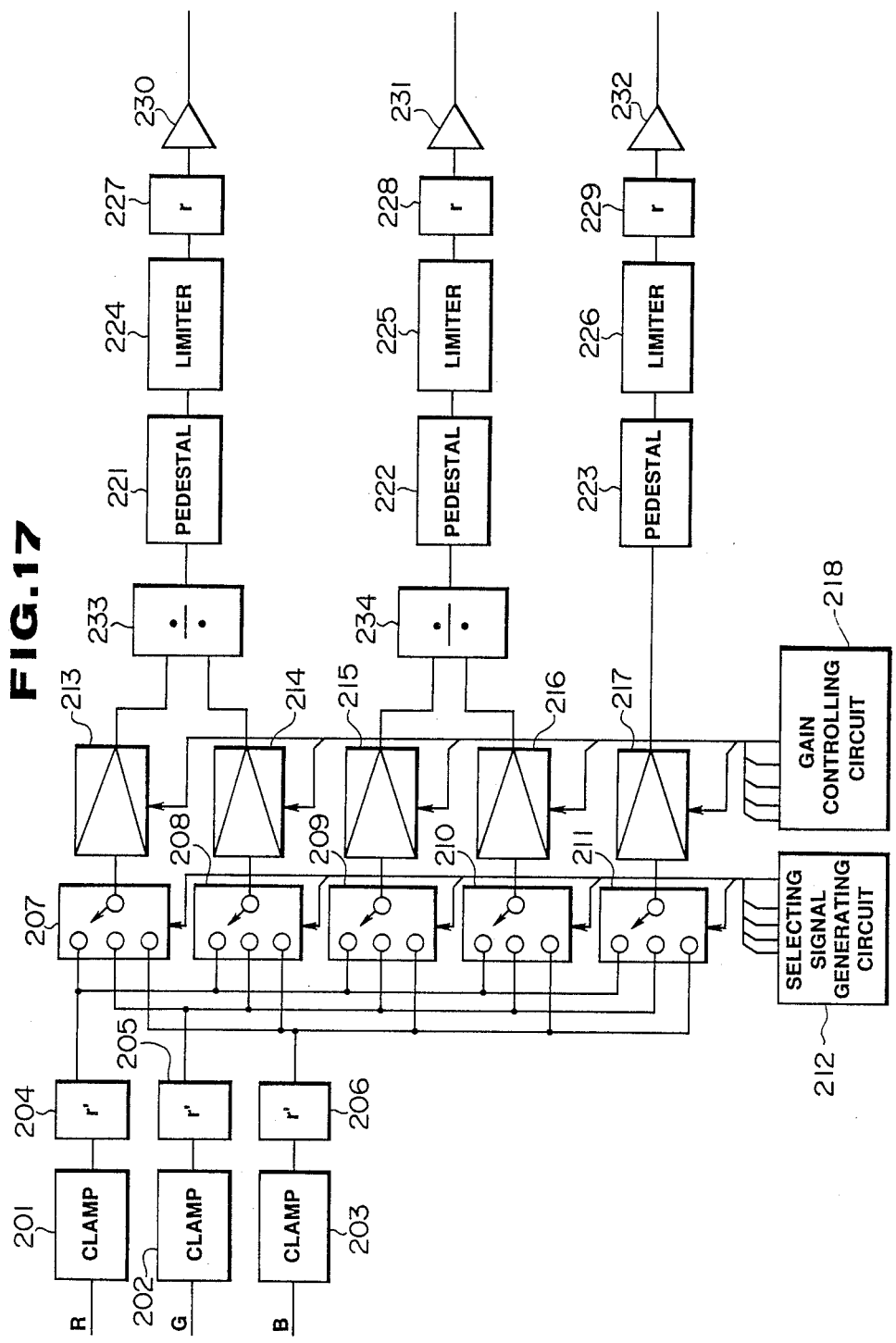
FIG. 17 is a block diagram showing a signal processing circuit which is an essential part of the sixth embodiment of the present invention.

The sixth embodiment of the present invention is shown in FIG. 17.

In this embodiment, division circuits 233 and 234 are provided instead of the differential amplifying circuits 219 and 220 in the fifth embodiment. The other formations are the same as in the fifth embodiment.

In this embodiment, by the same operation as in the fifth embodiment, a video signal selected by the selector circuit 207 is amplified at a designated amplifying rate by the gain controlling circuit 218 and is output from the variable gain amplifier 213. In the same manner, a video signal selected by the selector circuit 208 is amplified at an amplifying rate the same as or different from the amplifying rate of the above mentioned variable gain amplifier 213 by the gain controlling circuit 218 and is output from the variable gain amplifier 214.

The video signals output from the above mentioned variable gain amplifiers 213 and 214 are input into the division circuit 233 and the ratio of both video signals is calculated.

In the same manner, the respective video signals selected by the selector circuits 209 and 210 are amplified by the variable gain amplifiers 215 and 216 and are input into the division circuit 234. The ratio of both video signals is calculated by this division circuit 234.

The video signals output from the above mentioned division circuits 233 and 234 are set in the pedestal levels by the pedestal level setting circuits 221 and 222, are limited by the limiter circuits 224 and 225 to be signals only in a displayable range as visible signals or in a range of effective data, are γ-corrected by the γ-correcting circuits 227 and 228 to be displayed in the television monitor and are output through the buffer circuit 230 and 231.

The other operations are the same as in the fifth embodiment.

According to this embodiment, in addition to the effect of the fifth embodiment, by calculating the ratio between the two video signals, the influence of the brightness between the respective video signals by the distance can be canceled, the coloring matter variation on the mucous membrane surface can be enhanced without being influenced by a shadow or the like and there is an effect that the diagnosability will improve.

Figure 18:
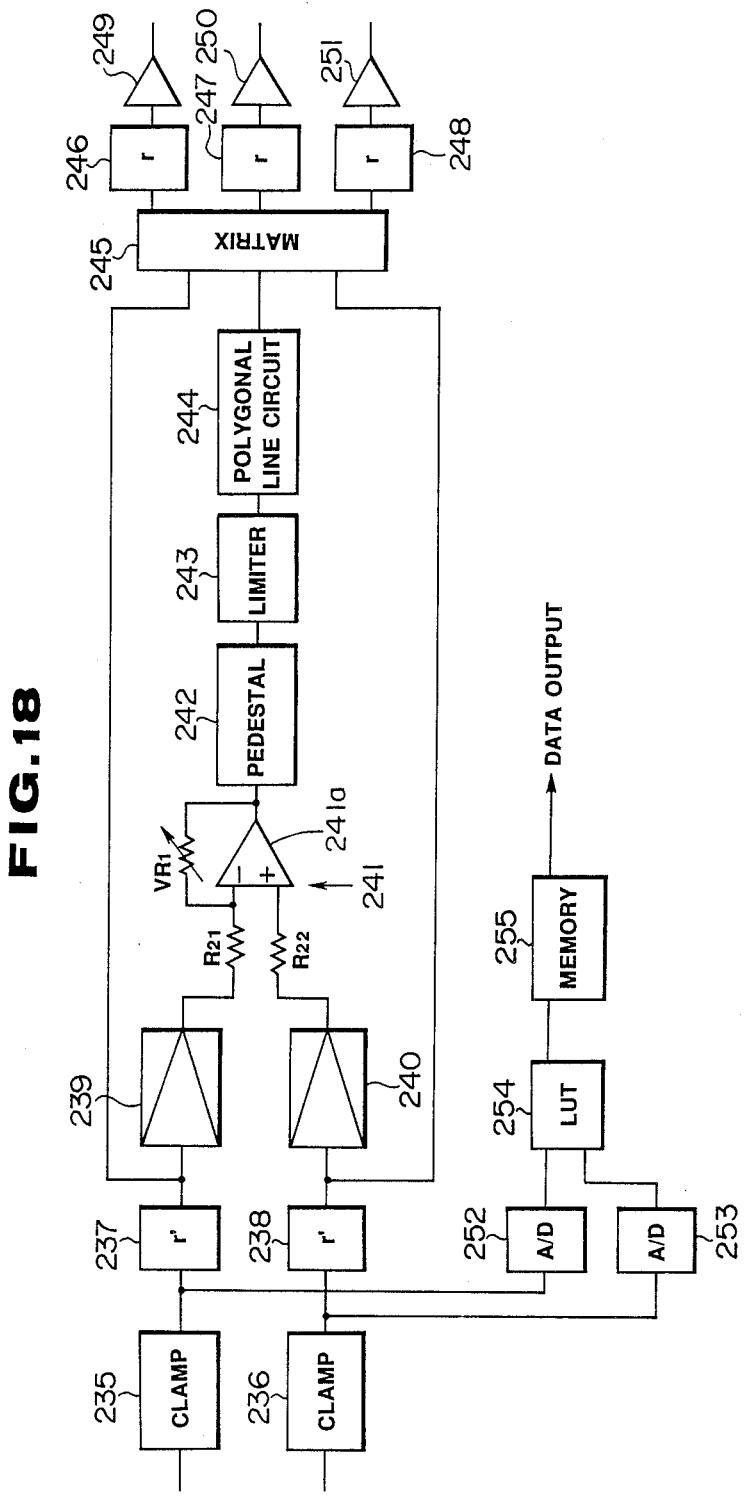
FIG. 18 is a block diagram showing a signal processing circuit which is an essential part of the seventh embodiment of the present invention.

The seventh embodiment of the present invention is shown in FIG. 18.

In this embodiment, two kinds of video signals among a plurality of video signals obtained by such endoscope apparatus as is shown in FIG. 14 or 15 are further input and processed in the signal processing circuit shown in FIG. 18.

This signal processing circuit is provided with clamping circuits 235 and 236 clamping input two kinds of video signals. The signals clamped by these clamping circuits 235 and 236 are input respectively into γ'-circuits 237 and 238 whereby the signal γ-corrected to be displayed in the television picture surface or the like in such endoscope apparatus as is shown in FIG. 14 or 15 is γ-corrected so that the video signal level and the brightness of the video image may be in a linear relation.

The video signals output from the above mentioned γ'-circuits 237 and 238 are amplified at a predetermined amplifying rate respectively by amplifiers 239 and 240. The respective video signals output from the above mentioned amplifiers 239 and 240 are input into a differential amplifying circuit 241 so that the difference between both video signals may be Operated. In the above mentioned differential amplifying circuit 241, the outputs of the amplifiers 239 and 240 are applied respectively through resistances $R_{21}$ and $R_{22}$ to the respective input ends of an operating amplifier $241a$ negatively fed back through a variable resistance $VR_1$. The output of the above mentioned differential amplifying circuit 241 is input into a pedestal level setting circuit 242 setting the pedestal level of the video signal. The output of the above mentioned pedestal level setting circuit 242 is input into a limiter circuit 243 defining the output level width of the video signal. The output of the above mentioned limiter circuit 243 is input into a polygonal line circuit 244 making the relation between the input level and output level non-linear.

The respective video signals from the above mentioned γ'-circuits 237 and 238 and polygonal line circuit 244 are input into a matrix circuit 245 distributing the three signals of R, G and B at respective predetermined ratios. The three signals output from this matrix circuit 245 are input respectively into γ-correcting circuits 246, 247 and 248 to be γ-corrected to be displayed in the television picture surface and the respective outputs of these γ-correcting circuits 246 to 248 are output through buffer circuits 249, 250 and 251 for outputting video signals.

Also, the video signals clamped by the above mentioned clamping circuits 235 and 236 are A/D-converted respectively by A/D converters 252 and 253 and the video signals output from these both A/D converters 252 and 253 are input into a look-up table (LUT) 254 in which the value of the difference after the logarithmic conversion of both video signals is memorized in response to the combination of the digital video signals from the above mentioned A/D converters 252 and 253. The operated picture image data output from the above mentioned look-up table 254 are memorized in a memory 255 so as to be able to be read out as required.

The operation of this embodiment shall be explained in the following.

In this embodiment, two kinds of picture image signals of such combination of a video signal near 800 nm large in the variation of the light absorbing degree after the ICG intravenous injection and a video signal above 900 nm small in the variation as is described, for example, in the first embodiment, such combination of a G signal large in the light absorption by hemoglobin in the blood and an R signal small in the variation of the light absorbing degree as is described in the third embodiment or a combination of a picture image signal in a wavelength range large in the light absorption at the time of dyeing with such coloring matter as methylene blue and a picture image signal in a wavelength range small in the absorption are input into the clamping circuits 235 and 236. By the way, the picture image signal of such wavelength range as is described above can be easily obtained by changing the transmitting characteristics of the respective filters of the rotary filter, for example, in the third embodiment.

The video signals clamped by the above mentioned clamping circuits 235 and 236 are γ'-corrected by the γ'-circuits 237 and 238, are then amplified at the respective amplifying rates by the amplifiers 239 and 240 to be operated at the optimum ratio and are then input into a differential amplifying circuit 241 and the level difference between the two kinds of picture images is operated.

The video signal produced by the operating process by the above mentioned differential amplifying circuit 241 is set in the pedestal level by a pedestal level setting circuit 242 so that the level difference between the above mentioned two kinds of picture images may be displayed to be maximum and the average value of the signal levels may be substantially equal to the average value of the video signals at the displaying time. The video signal having had this pedestal level adjusted is limited by a limiter circuit 243 to be within the displayable signal level range. The video signal output from this limiter circuit is input into a polygonal line circuit 244. This polygonal line circuit 244 is to set the input-output relation so that the amplifying rate may be different in response to the input level. For example, when the amplifying rate is elevated at the low level time to be higher than at the high level time, the variation of the low level will be able to be enhanced. When the input-output relation in the polygonal line circuit 244 is made to have an S-like curve so as to enhance the level near the middle, the video level will be able to be enhanced near the middle.

The respective video signals from the γ'-circuits 237 and 238 and polygonal line circuit 244 are input into a matrix circuit 245 and are distributed to R, G and B signals at respectively predetermined ratios. For example, in case the signals output from the polygonal line circuit 244 are made bright and dark signals, the respective ratios to R, G and B of the output signals of this polygonal line circuit 244 will be made 3:6:1. Also, the output of the γ'-circuit 237 can be made a luminance signal and the other outputs can be made color signals. When the ratios of the input signal to the R, G and B signals at the outputting time of the matrix circuit 245 are varied, an enhancing effect higher in the sight than in the case of alotting the respective output signals of the γ'-circuits 237 and 238 and polygonal line circuit 244 to any of R, G and B will be able to be obtained.

The three signals output from the above mentioned matrix circuit 245 are γ-corrected by the γ-correcting circuits 246, 247 and 248 to be displayed in the television monitor and are output through the buffer circuits 249, 250 and 251.

On the other hand, the video signals from the clamping circuits 235 and 236 are A/D-converted by A/D-converters 252 and 253 and are input into a look-up table 254. The coloring matter concentration data as a result of the γ'-correction, logarithmic conversion and calculation of the coefficient of the level correction between the respective channels to calculate the coloring matter concentration in the living body by the signal level difference between the two kinds of video images are memorized in this look-up table 254 and the coloring matter concentration data contained in the address designated by the level of the A/D converters 252 and 253 are output from this look-up table 254. These data are memorized in a memory 255 and the above mentioned coloring matter concentration data value can be read out and measured from this memory 255.

Thus, according to this embodiment, the difference between the two kinds of picture images with the coloring matter concentration variation can be processed to be enhanced as a color picture image, thereby a slight color difference variation can be detected and there is an effect of improving the diagnosability.

By the way, the present invention is not limited to the above mentioned respective embodiments and, for example, the endoscope observing part may be observed with a through illumination. In this case, the living body may be illuminated from outside or only the tissue may be illuminated with the light led into the living body.

Also, the present invention can be applied not only to an electronic endoscope having a solid state imaging device in the tip part of the insertable part but also to an endoscope apparatus used as connected with an externally fitted television camera having such solid state imaging device as a CCD in the eyepiece part of such endoscope with which a naked eye observation is possible as a fiber scope or by replacing the eyepiece part.

As explained above, according to the present invention, at least one new image is formed on the basis of the images of at least two wavelength ranges among the images of the respective wavelength ranges separated in the wavelengths by a wavelength separating means and an observed image is formed of at least one image including this new image. Therefore, there is an effect that the feature of the object part can be more enhanced. Further, at least one new image is formed by enhancing at least one image among the images of the respective wavelength ranges in response to the variation of the image of at least another wavelength range and the observed image is formed of this enhanced image. Therefore, there are effects that the tone observation similar to the ordinary observation is possible and the feature of the object part can be more enhanced. By such effects, the living body information difficult or impossible to observe with the ordinary color picture image can be obtained and the diagnosability can be improved.

It is apparent that, in this invention, working modes different in a wide range can be formed on the basis of this invention without deviating from the spirit and scope of the invention. This invention is not restricted by its specific working modes except being limited by the appended claims.

What is claimed is:

1. An endoscope apparatus comprising:
   an endoscope having at least an image forming optical system;
   a wavelength separating means for separating an observed object image into images of a plurality of wavelength ranges;
   an imaging means for imaging the images of the respective wavelength ranges formed by said image forming optical system and separated by said wavelength separating means; and
   a signal processing means for forming at least one new image on the basis of the images of at least two wavelength ranges among said images of the respective wavelength ranges imaged by said imaging means and forming an observed image on the basis of at least one image including said new image.

2. An endoscope apparatus according to claim 1 wherein said wavelength separating means has an illuminating means for sequentially radiating illuminating lights of a plurality of wavelength ranges to the object.

3. An endoscope apparatus according to claim 1 wherein said wavelength separating means has a color separating filter provided on the front surface of said imaging means.

4. An endoscope apparatus according to claim 1 wherein said imaging means has a solid state imaging device arranged in the image forming position of said image forming optical system in the tip part of said endoscope.

5. An endoscope apparatus according to claim 1 wherein said signal processing means forms said observed image by a matrix operation using a signal of the images of two wavelength ranges among said images of the respective wavelength ranges imaged by said imaging means and a signal of the level difference of the images of said two wavelength ranges.

6. An endoscope apparatus according to claim 5 wherein said two wavelength ranges are wavelength ranges in which a difference is produced in the light absorbing degree of a specific coloring matter.

7. An endoscope apparatus according to claim 1 wherein said signal processing means forms one new image constituting said observed image by the level difference of the images of two wavelength ranges among said images of the respective wavelength ranges imaged by said imaging means.

8. An endoscope apparatus according to claim 1 wherein said signal processing means forms one new image constituting said observed image by the ratio of the levels of the images of two wavelength ranges among said images of the respective wavelength ranges imaged by said imaging means.

9. An endoscope apparatus according to claim 7 or 8 wherein said two wavelength ranges are a wavelength range of green and a wavelength range of red.

10. An endoscope apparatus according to claim 7 or 8 wherein said two wavelength ranges are a wavelength range of green and a wavelength range of blue.

11. An endoscope apparatus according to claim 1 wherein said signal processing means has an observed image forming means for forming an observed image from the images of the respective wavelength ranges imaged by said imaging means and an enhancing means for forming at least said new image by enhancing the image of the wavelength range constituting said observed image formed by said observed image forming means in response to the variation of at least one of the images of said respective wavelength ranges imaged by said imaging means.

12. An endoscope apparatus according to claim 4 wherein said enhancing means enhances the luminance of said observed image in response to the variation of at least one of said images of the respective wavelength ranges imaged by said imaging means.

13. An endoscope apparatus according to claim 11 wherein said enhancing means has a means for multiplying the signal of the image of the wavelength range constituting said observed image and the signal of at least one image among said images of the respective wavelength ranges imaged by said imaging means by each other.

14. An endoscope apparatus according to claim 11 wherein said enhancing means has a gain variable amplifier inputting the signal of the image of the wavelength range constituting said observed image and the gain of said gain variable amplifier is controlled by the signal of at least one image among said images of the respective wavelength ranges imaged by said imaging means.

15. An endoscope apparatus according to claim 11 wherein said enhancing means has a means of adding the signal of the wavelength range constituting said observed image and the signal of at least one image among said images of the respective wavelength ranges imaged by said imaging means.

16. An endoscope apparatus according to claim 11 wherein said wavelength separating means separates the object image into images of three wavelength ranges capable of forming a color picture image and images of two wavelength ranges different from said three wavelength ranges, said observed image forming means formes an observed image from said image of said three wavelength ranges and said enhancing means enhances the image of the wavelength range constituting said observed image formed by said observed image forming means in response to the level difference of said images of said two wavelength ranges.

17. An endoscope apparatus according to claim 16 wherein said two wavelength ranges are wavelength ranges in which a difference is produced in the light absorbing degree of a specific coloring matter.

18. An endoscope apparatus according to claim 11 wherein said wavelength separating means separates the object image into images of three wavelength ranges capable of forming a color picture image and an image of one wavelength range different from said three wavelength ranges, said observed image forming means forms an observed image from said images of said three wavelength ranges and said enhancing means enhances the image of the wavelength range constituting said observed image formed by said observed image forming means in response to the variation of said image of said one wavelength range.

19. An endoscope apparatus according to claim 18 wherein said one wavelength range is near the wavelength range in which the light absorbing degree of a specific coloring matter is the largest.

20. An endoscope apparatus according to claim 11 wherein said wavelength separating means separates the object image into images of three wavelength ranges capable of forming a color picture image, said observed image forming means forms an observed image from said images of said three wavelength ranges and said enhancing means enhances the image of the wavelength range constituting said observed image formed by said observed image forming means in response to the level difference of the images of two wavelength ranges among said image of said three wavelength ranges.

21. An endoscope apparatus according to claim 20 wherein said two wavelength ranges are wavelength ranges in which a difference is produced in the light absorbing degree of a specific coloring matter.

22. An endoscope apparatus according to claim 11 wherein said wavelength separating means separates the object image into images of three wavelength ranges capable of constituting a color picture image, said observed image forming means forms an observed image from said images of said three wavelength ranges and said enhancing means enhances the image of the wavelength range constituting said observed image formed by said observed image forming means in response to the variation of the image of one wavelength range among said images of said three wavelength ranges.

23. An endoscope apparatus according to claim 22 wherein said one wavelength range is near the wavelength range in which the light absorbing degree of a specific coloring matter is the largest.

* * * * *